United States Patent
Cheng et al.

(10) Patent No.: US 8,308,924 B2
(45) Date of Patent: Nov. 13, 2012

(54) ENZYME ELECTRODE AND METHOD FOR PRODUCING THE SAME

(75) Inventors: Chean-Yeh Cheng, Tao-Yuan (TW); Kuo-Chung Chang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 250 days.

(21) Appl. No.: 12/860,806

(22) Filed: Aug. 20, 2010

(65) Prior Publication Data

US 2010/0311143 A1    Dec. 9, 2010

Related U.S. Application Data

(63) Continuation-in-part of application No. 12/421,565, filed on Apr. 9, 2009, now Pat. No. 8,172,996.

(51) Int. Cl.
*G01N 27/327* (2006.01)
(52) U.S. Cl. .............. 204/403.11; 204/403.14; 427/2.13
(58) Field of Classification Search .............. 204/403.01, 204/403.11, 403.14; 427/2.13
See application file for complete search history.

(56) References Cited

U.S. PATENT DOCUMENTS 5,286,364 A * 2/1994 Yacynych et al. .............. 205/83

OTHER PUBLICATIONS

Imamura et al, Sensors and Actuators B 24-25, 1995, pp. 113-116.*
Schlereth et al, Electroanalysis 7(1), 1995, pp. 46-54.*
Molinero et al, Journal of Electroanalytical Chemistry 445, 1998, pp. 17-25.*
Hasunuma et al, Analytical Chemistry 76, 2004, pp. 1500-1506.*
Carbodiimide entry from Wikipedia.org, Sep. 2012.*

* cited by examiner

*Primary Examiner* — Kaj K Olsen
(74) *Attorney, Agent, or Firm* — Stout, Uxa, Buyan & Mullins, LLP

(57) ABSTRACT

The present invention discloses an enzyme electrode and its producing method, which comprises: providing a substrate with a carbon surface; forming a gold surface on the carbon surface and thus forming an electrode; covalently bonding a mediator containing an aldehyde group to the electrode; and covalently bonding a glucose oxidase to the electrode.

20 Claims, 7 Drawing Sheets

ENZYME ELECTRODE AND METHOD FOR PRODUCING THE SAME

CROSS-REFERENCE TO RELATED APPLICATIONS

This application is a continuation-in-part of co-pending application Ser. No. 12/421,565, filed Apr. 9, 2009, which claims priority to Taiwan Patent Application No. 098106428, filed Feb. 27, 2009, the entire contents both of which are incorporated herein by reference.

BACKGROUND OF THE INVENTION

1. Field of the Invention

The present invention relates to an enzyme electrode and a method for producing the enzyme electrode.

2. Description of Related Art

Carbohydrate analysis can be performed by methods including optical rotation (Beychok and Kabat, 1965), colorimetry (Thomas and Dutcher, 1924), enzyme electrode (Qiu et al., 2009; Sun et al., 2008; Zhang et al., 2005), and high-performance liquid chromatography (HPLC) with various kinds of detector (Cai et al., 2005; Cheng and Chang, 2007; Cheng, et al., 2006; Kauppila et al., 2008; Qian et al., 2008; Raessler et al., 2008). Scientists used HPLC most for the simultaneous determination of several carbohydrates with good accuracy, precision, and sensitivity. However, in spite of the advantages of HPLC, the instrument for HPLC is bulky and expensive and the analysis time is usually lengthy (Cheng et al., 2010). Therefore, for many clinical applications such as the glucose monitoring for diabetes HPLC is not an ideal method to use. In recent years, the development of enzyme electrode method is seen to be a better technique for specific carbohydrate analysis by its advantages such as substrate specificity, easy operation, low cost, portable instrumentation, and faster analysis over the HPLC method (Qian et al., 2008).

Clark and Lyons developed the first generation of glucose enzyme electrode, and Schlapfer improved it by replacing oxygen with artificial mediator for eliminating the dependence of oxygen in the air. (Wang, 2008). Since then, ferrocene and its derivatives were used extensively as the artificial redox mediator (Escorcia and Dhirani, 2007; Qian et al., 2008; Wang and Du, 2004) for glucose enzyme electrode with their various desirable properties, e.g., a relatively low molecular mass, reversibility, regeneration at low potential, and generation of stable redox forms (Fernández and Carrero, 2005). Typically, the mediator is dissolved in an electrolyte for glucose analysis. However, ferrocene and its derivatives are carcinogenic and this property makes them not suitable for a lot of applications provided that they are disposed freely to the environment. One simple method to overcome this drawback is its immobilization to the electrode. Qiu and co-workers (2009) have reported an amperometric sensor from ferrocene carboxaldehyde directly and physically adsorbed on multiwalled carbon nanotubes for the determination of glucose. Reagentless enzyme-based glassy carbon electrode biosensor with a ferrocene-branched chitosan matrix for glucose analysis was also developed by Sun and co-workers (Yang et al., 2007).

Although many methods such as physical adsorption, cross-linking, and encapsulation have been disclosed to improve the immobilization of enzyme and even mediator to the electrode, so far it is still needed to provide an enzyme electrode with excellent accuracy, wide detectable concentration range, good stability, and long-term reusable capability.

In another aspect, the technique of flow injection analysis (FIA) was developed in 1976 by Denmark's scientists Ruzicka and Hansen (Zhi, 1998). Due to the advantages of fast continuous analysis, simplicity, and low cost, this technique is proved to be highly useful for practical applications in many fields, e.g., environmental monitoring, process analytical chemistry or clinical diagnostics (Thomaidis and Georgiou, 1999; Wang and Chen, 1995). FIA can be carried out either off-line or on-line mode; however, off-line FIA is usually tedious and may cause sample loss during sample transfer (Cheng and Chang, 2007). On-line FIA is thus used to solve these problems and to show the in-time monitoring ability. In recent years, the on-line FIA monitoring of glucose with biosensor in biological system (Kumar et al., 2001; Nandakumar et al., 1999) was usually coupled with microdialysis for sampling (Gramsbergen et al., 2004; Rhemrev-Boom et al., 2001; Yao et al., 2004). Accordingly, a need is arisen in the art to develop other types of sampling device coupled to on-line FIA that are more convenient to use.

REFERENCES

Asav, E., Akyilmaz, E., 2010. Biosens. Bioelectron. 25, 1014-1018.
Barsan, M. M., Klinčar, J., Batič, M., Brett, C. M. A., 2007. Talanta 71, 1893-1900.
Beychok, S., Kabat, E. A., 1965. Biochemistry 4, 2565-2574.
Cai, Y., Liu, J., Shi, Y., Liang, L., Mou, S., 2005. J. Chromatogr. A 1085, 98-103.
Cheng, C., Chang, K.-C., 2007. Anal. Sci. 23, 305-310.
Cheng, C., Chen, C.-S., Hsieh, P.-H., 2010. J. Chromatogr. A 1217, 2104-2110.
Cheng, C., Tsai, H.-R., Chang, K.-C., 2006. J. Chromatogr. A 1119, 188-196.
Escorcia, A., Dhirani, A.-A., 2007. J. Electroanal. Chem. 601, 260-268.
Fernández, L., Carrero, H., 2005. Electrochim. Acta 50, 1233-1240.
Ghica, M. E., Brett, C. M. A., 2006. Electroanalysis 18, 748-756.
Gramsbergen, J. B., Skjøth-Rasmussen, J., Rasmussen, C., Lambertsen, K. L., 2004. J. Neurosci. Methods 140, 93-101.
Harris, D. C., 2007. Quantitative chemical analysis, $7^{th}$ ed., W. H. Freeman and Company, New York, p. 87-90.
Kauppila, T. J., Talaty, N., Jackson, A. U., Kotiaho, T.; Kostiainen, R., Cooks, R. G., 2008. Chem. Commun., 2674-2676.
Kumar, M. A., Thakur, M. S., Senthuran, A., Senthuran, V., Karanth, N. G., Hatti-Kaul, R., Mattiasson, B., 2001. World J. Microbio. Biotechnol. 17, 23-29.
Liu, Y., Chu, Z., Zhang, Y., Jin, W., 2009. Electrochim. Acta 54, 7490-7494.
Miller, J. N., Miller, J. C., 2000. Statistics and Chemometrics for Analytical Chemistry, $4^{th}$ ed., Pearson Education Limited, England, p. 126-130.
Nandakumar, M. P., Lali, A. M., Mattiasson, B., 1999. Bioseparation 8, 229-235.
Pijanowska, D. G., Sprenkels, A. J., Olthuis, W., Bergveld, P., 2003. Sens. Actuators B 91, 98-102.
Qian, W. L., Khan, Z., Watson, D. G., Fearnley, J., 2008. J. Food Composit. Anal. 21, 78-83.
Qiu, J.-D., Zhou, W.-M., Guo, J., Wang, R., Liang, R.-P., 2009. Anal. Biochem. 385, 264-269.
Raessler, M., Wissuwa, B., Breul, A., Unger, W., Grimm, T., 2008. J. Agric. Food Chem. 56, 7649-7654.

Rhemrev-Boom, M. M., Jonker, M. A., Venema, K., Jobst, G., Tiessen, R., Korf, J., 2001. Analyst 126, 1073-1079.
Shimokawa, T., Ishida, M., Yoshida, S., Nojiri, M., 2009. Bioresour. Technol. 100, 6651-6654.
Sun, Y., Wang, H., Sun, C., 2008. Biosens. Bioelectron. 24, 22-28.
Tan, X.-C., Tian, Y.-X., Cai, P.-X., Zou, X.-Y., 2005. Anal. Bioanal. Chem. 381, 500-507.
Thomaidis, N. S., Georgiou, C. A., 1999. Lab. Autom. Inf. Manage. 34, 101-114.
Thomas, W., Dutcher, R. A., 1924. J. Am. Chem. Soc. 46, 1662-1669.
Tsai, M.-C., Tsai, Y.-C., 2009. Sens. Actuators, B 141, 592-598.
Wang, J., 2008. Chem. Rev. 108, 814-825.
Wang, J., Chen, L., 1995. Talanta 42, 385-389.
Wang, S., Du, D., 2004. Sens. Actuators B 97, 373-378.
Wu, C.-C., Cheng, C., 2005. J. Chin Chem. Soc. 52, 85-95.
Yan, W., Feng, X., Chen, X., Hou, W., Zhu, J.-J., 2008. Biosens. Bioelectron. 23, 925-931.
Yang, L., Ren, X., Tang, F., Zhang, L., 2009. Biosens. Bioelectron. 25, 889-895.
Yang, W., Wang, J., Zhao, S., Sun, Y., Sun, C., 2006. Electrochem. Commun. 8, 665-672.
Yang, W., Zhou, H., Sun, C., 2007. Macromol. Rapid Commun. 28, 265-270.
Yao, T., Yano, T., Nishino, H., 2004. Anal. Chimi Acta 510, 53-59.
Zhang, S., Wang, N., Yu, H., Niu, Y., Sun, C., 2005. Bioelectrochemistry 67, 15-22.
Zhi, Z.-L., 1998. Trends Anal. Chem. 17, 411-417.

SUMMARY OF THE INVENTION

An object of the present invention is to provide an enzyme electrode with excellent accuracy, wide detectable concentration range, good stability, and long-term reusable capability.

Accordingly, one embodiment of the present invention provides a method for producing an enzyme electrode, comprising: providing a substrate with a carbon surface; forming a gold surface on the carbon surface and thus forming an electrode; covalently bonding a mediator containing an aldehyde group to the electrode; and covalently bonding a glucose oxidase to the electrode.

Accordingly, one embodiment of the present invention provides a method for producing an enzyme electrode, comprising: providing a substrate with a carbon surface; forming a gold surface on the carbon surface and thus forming an electrode; modifying the gold surface by L-cysteine to covalently bond the gold particles of the gold surface and the sulfhydryl group of L-cysteine, thereby forming a first electrode with a first modified surface; covalently bonding a mediator containing an aldehyde group to the amino group of the L-cysteine and thus resulting in a Schiff base, thereby forming a second electrode with a second modified surface; modifying the second modified surface by N,N'-dicyclohexylcarbodiimide, therefore the L-cysteine and the N,N'-dicyclohexylcarbodiimide being dehydrated to form a covalent bond, thereby forming a third electrode with a third modified surface; and contacting the third modified surface with glucose oxidase, an amide bond being formed between the L-cysteine group of the third modified surface and the glucose oxidase, thereby forming a fourth electrode with a fourth modified surface.

Accordingly, one embodiment of the present invention provides an enzyme electrode, comprising: a substrate with a carbon surface; a gold surface deposited on at least a portion of the carbon surface; an amino acid including an amine group, a carboxyl group, and a thiol group, the amino acid binding to the gold surface through the thiol group; a mediator containing an aldehyde group, wherein the mediator and the amino group form a Schiff base; and a glucose oxidase binding to the carboxyl group of the amino acid through a peptide-coupling reagent with a diimide structure, wherein the glucose oxidase and the peptide-coupling reagent form an amide bond.

Accordingly, one embodiment of the present invention provides an enzyme electrode, comprising: a substrate structure, the substrate structure comprising a pencil lead, a carbon layer covering the pencil lead, and a gold layer covering the carbon layer; and a modified structure, the modified structure being chemically bounded with the gold layer, the modified structure comprising a L-cysteine group, a glucose oxidase group, and a mediator group containing an aldehyde group, an Au—S covalent bond being formed between the gold layer and the L-cysteine group, an amide bond being covalently bounded between the L-cysteine group and the glucose oxidase group, a carbon-nitrogen double bond being formed between the L-cysteine group and the mediator group.

DESCRIPTION OF THE PREFERRED EMBODIMENT

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not described in detail in order not to unnecessarily obscure the present invention. While drawings are illustrated in details, it is appreciated that the quantity of the disclosed components may be greater or less than that disclosed, except expressly restricting the amount of the components. Wherever possible, the same or similar reference numbers are used in drawings and the description to refer to the same or like parts.

Figure 1:
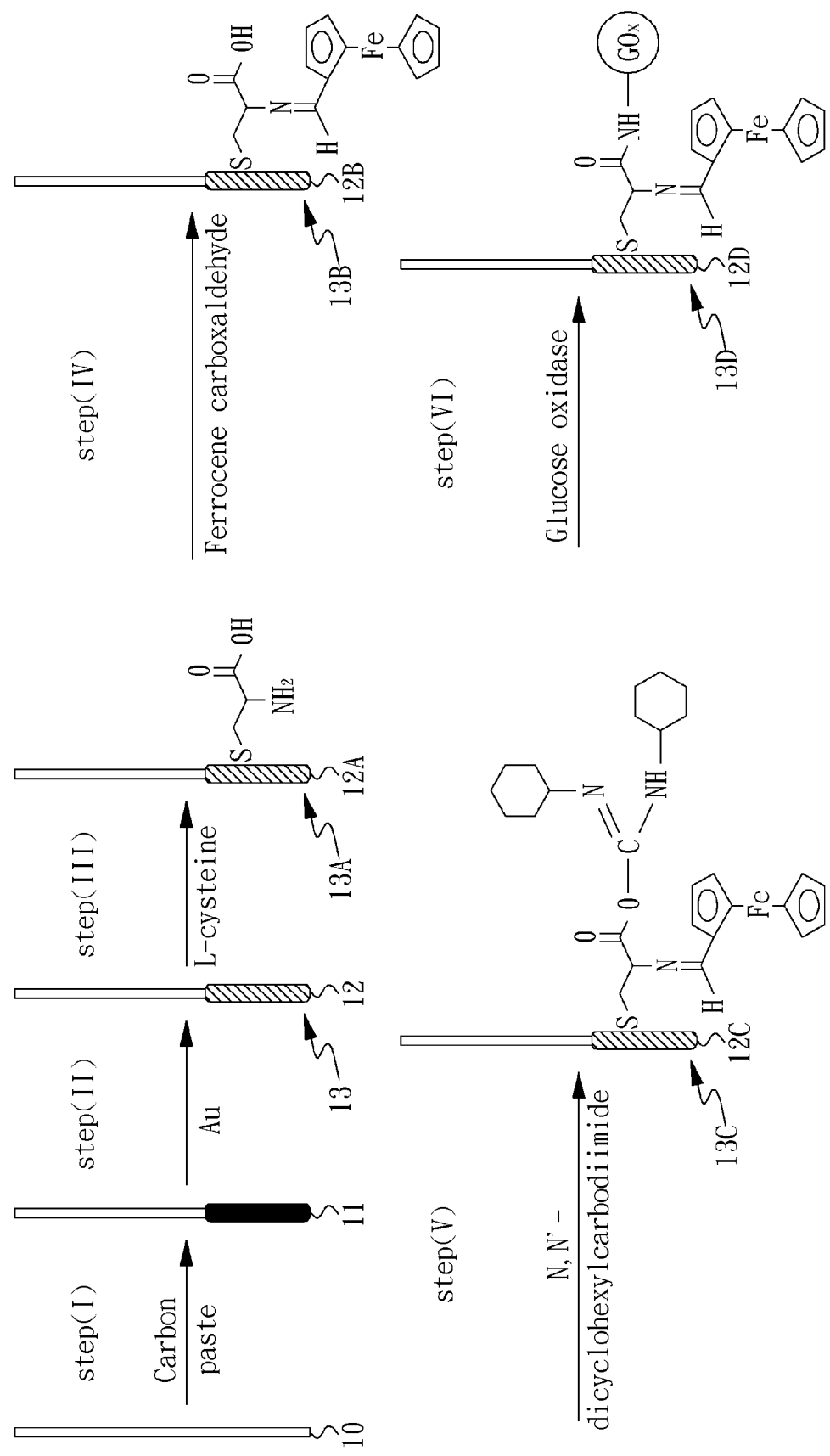
FIG. 1 shows a method for forming an enzyme electrode according to a preferred embodiment of the present invention.

FIG. 1 shows a method for forming an enzyme electrode according to a preferred embodiment of the present invention, which comprises following six steps. In step (I), a pencil lead 10 is coated with a layer of carbon paste 11 with a height about 5 cm at 120° C. for 10 minutes. This layer of carbon paste 11 is necessary to avoid interference of the enzyme activity from the impurities in the pencil lead 10. Higher enzyme activity can be expected if higher purity of the carbon paste 11 is employed. In step (II), tetrachloroaurate is reduced in an aqueous solution with an applied voltage of 0.2 V so as to deposit gold particles on the surface of the coated carbon paste 11 in height about 0.8 cm by electrodeposition at 28° C. for 2 hours, resulting in an electrode 13 with a gold surface 12. Then, the electrode 13 may be rinsed with water to remove the unreduced gold compounds at 28° C. In step (III), the electrode 13 is immersed in a 20 mM L-cysteine solution for 1 hour at 25° C. to covalently bond the gold particles and the sulphydryl group (—SH, also referred to as thiol group) of L-cysteine, resulting in a first electrode 13A with a first modified surface 12A. The first electrode 13A may then be thoroughly rinsed with deionized distilled water at 25° C. to remove physically adsorbed L-cysteine. In step (IV), the first electrode 13A is immersed in the 0.1 mM Ferrocene carboxaldehyde (i.e., FcAld, dissolved in EtOH/HCl, 99.5/0.5, v/v) at 75° C. for 1 hour to covalently bond the mediator (FcAld) and the amino group of the L-cysteine and thus form an Schiff base, resulting a second electrode 13B with a second modified surface 12B. Then the second electrode 13B may be rinsed with deionized distilled water at the same temperature (75° C.). During step (V), the second electrode 13B is immersed in the 5.0 mM N,N'-dicyclohexylcarbodiimide methanol solution for 1 hour at 40° C. to chemically bind the N,N'-dicyclohexylcarbodiimide through the carboxyl group of the L-cysteine by a dehydration reaction, resulting in a third electrode 13C with a third modified surface 12C. The adsorbed diimide may be removed sequentially with methanol and deionized distilled water at 40° C. for about 5 minutes. In step (VI), the third electrode 13C is dipped in 50 µM glucose oxidase solution prepared with 0.1 M pH 7.0 sodium phosphate buffer (NaPB) solution at 25° C. for 24 hours to bind glucose oxidase, resulting a fourth electrode 13D with a fourth modified surface 12D, where an amide bond or peptide bond is formed between the L-cysteine group of the third modified surface 12C and the glucose oxidase and thus the enzyme glucose oxidase is chemically bonded on the electrode surface. Finally, the fourth electrode 13D is the wanted enzyme electrode and may be stored in 0.1 M pH 7.0 NaPB at 4° C. for later glucose analyses.

Modifications may be made on the above-mentioned embodiment. For example, the pencil lead coated with carbon paste may be replaced by a substrate with a carbon surface, and the carbon surface may occupy a portion or the whole surface of the substrate. Step (IV) may be performed after step (V) or step (VI). In addition, the substrate may be rod-shaped, slice-shaped or other configurations. The substrate may be made of any metal or non-metal materials. Other methods such as deposition, ink-inject, or screen-printing method may be employed for forming the gold surface 12. Other amino acids including an amino group, a carboxyl group, and a thiol group in the side chain, may replace the L-cysteine. Other peptide coupling reagents with a diimide structure may replace N,N'-dicyclohexylcarbodiimide. And other mediators containing an aldehyde group may replace ferrocene carboxaldehyde.

Experiments are made for qualifying the enzyme electrode produced by the present invention. In an embodiment, after an enzyme electrode has been successfully made with covalently bonded redox mediator ferrocene carboxaldehyde and glucose oxidase, the enzyme electrode is used to establish an on-line FIA system for long-term continuously monitoring glucose level of products of a bioreactor.

Figure 2A:
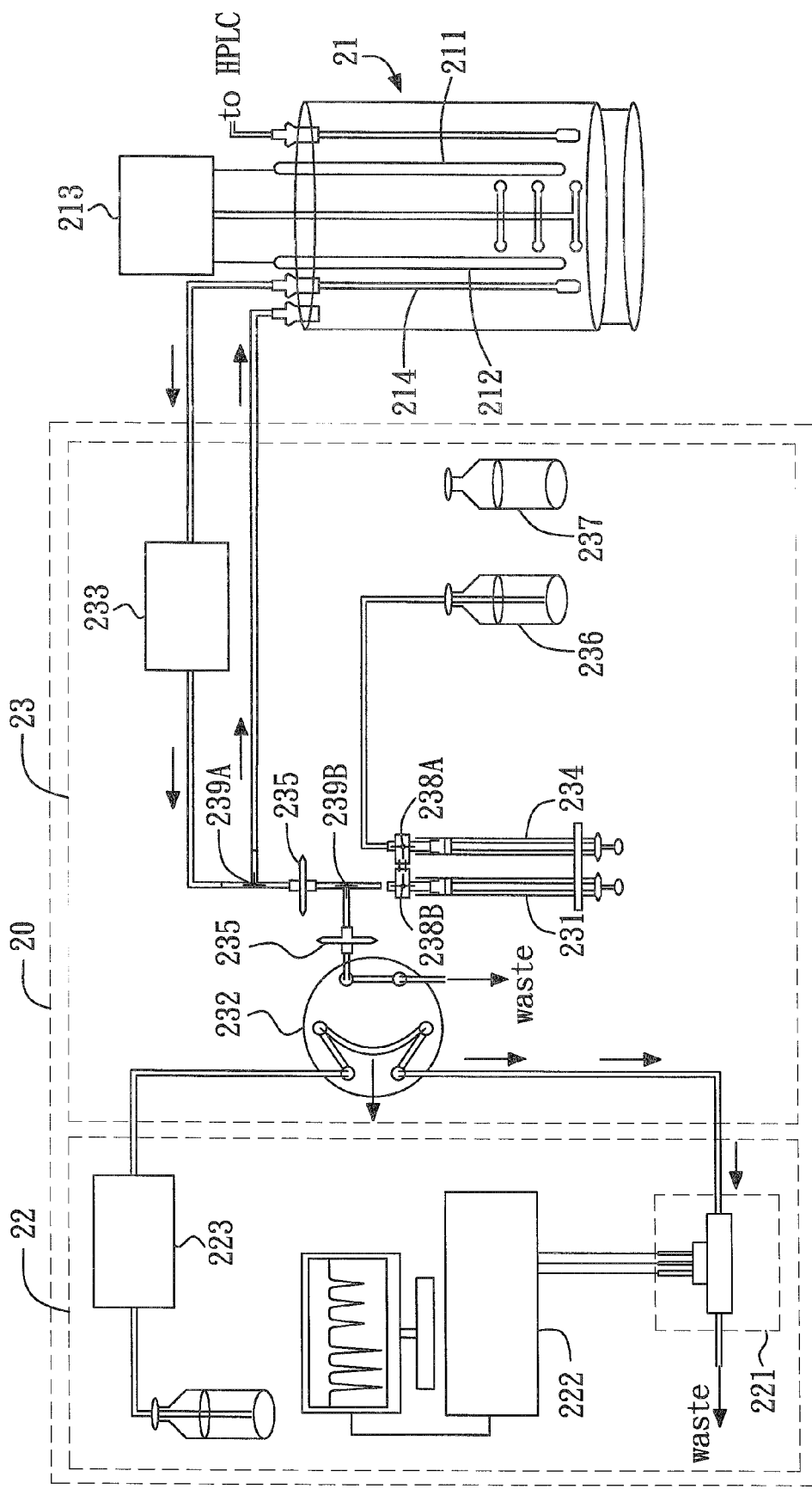
FIG. 2A shows a schematic diagram of an FIA system for on-line determination of glucose level of products of a bioreactor, according to an embodiment of the present invention.

FIG. 2A shows a schematic diagram of an FIA system for the on-line determination of glucose level of products of a bioreactor, according to an embodiment of the present invention. The FIA system 20 is coupled to a bioreactor 21 through an electrochemical analysis subsystem 22 and a stopped-flow sampling and injection subsystem 23 to analyze products of the bioreactor 21. In this embodiment, the products containing glucose are obtained by the hydrolysis of waste bamboo chopsticks with immobilized cellulase. The analytical efficiency of the glucose content with the on-line FIA enzyme electrode method is also compared with an on-line HPLC-RI method.

Figure 2B:
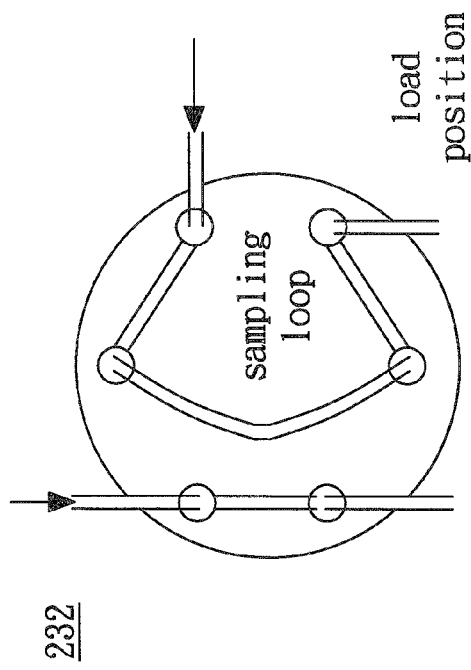
FIG. 2B shows the six-port injection valve of the FIA system of FIG. 2A.
Figure 2B:
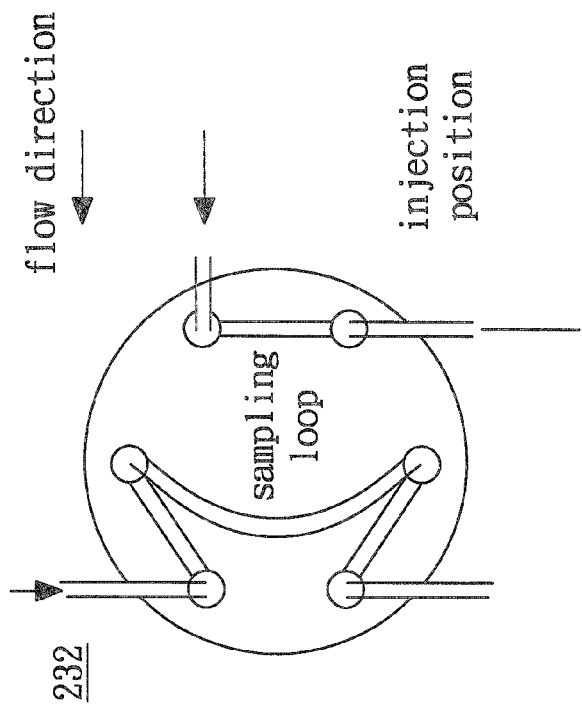

The determination of the glucose content in the immobilized enzyme hydrolysate of waste bamboo chopsticks is performed by a single standard addition method to compensate for the decay of the glucose sensor electrode and eliminate the matrix effect. During the hydrolysis period, the hydrolysate is taken on-line from the bioreactor 21 by the peristaltic pump 233 every 4 hours in the first 16 hours reaction period and every 8 hours for the rest of the reaction period. The immobilized enzyme hydrolysate drawn from the bioreactor 21 is filtered on-line through syringe filters 235. The sampling, loading, and injection procedures of the hydrolysate are described as follows: (1) two milliliters of the sample from the bioreactor 21 are drawn manually using the sample syringe 231 of the stopped-flow sampling subsystem 23; (2) a six-port injection valve 232 is positioned at the load position (see FIG. 2B), and one milliliter of the sample is loaded to the 50 µl sampling loop of the six-port injection valve 232; (3) the injection valve 232 is switched to the injection position (see FIG. 2B), to inject the loaded 50 µL sample through the help of peristaltic pump 223, such that the sample is analyzed by the electrochemical analysis subsystem 22; (4) the six-port injection valve 232 is switched back to load position; (5) one milliliter glucose standard solution 236 is drawn manually into the standard syringe 234; (6) 0.1 mL glucose standard solution 236 is drawn manually from the standard syringe 234 to the sample syringe 231 through the three-port valve 238A and 238B; (7) about 1.1 mL of the spiked sample solution are manually loaded from the sample syringe 231 to the 50 µL sampling loop through the three-port valve 238B; (8) the six-port injection valve 232 is turn to the inject position, such that the spiked sample is analyzed by the electrochemical analysis subsystem 22; (9)

the six-port valve 232 is then switched back to the load position after the completion of the electrochemical analysis; (10) the glucose standard solution is replaced with deionized distilled water 237 to wash the two syringes 231/234 of the stopped-flow sampling subsystem 23 making the stopped-flow sampling subsystem 23 ready for the next analysis. Note that the concentration of the glucose standard solution added on-line to the hydrolysate sample during procedure (6) is varied to let an increase of the measured current to about 1.5 times the measured current of the unspiked hydrolysate sample. Then, the amount of glucose in the immobilized enzyme hydrolysate can be calculated with corresponding standard addition equations (Harris, 2007). The quantification of glucose produced is also determined by the on-line HPLC-RI system with on-line external standard calibration curve method (Cheng and Chang, 2007).

Figure 2C:
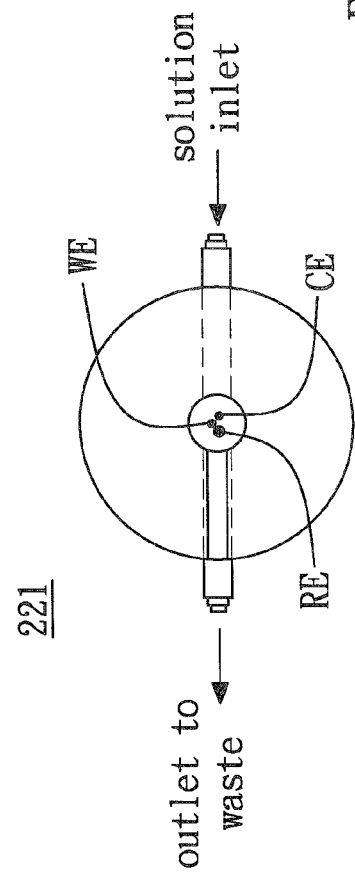
FIG. 2C is a schematic diagram of the top-view and the side-view of the specific designed three-electrode flow cell of the FIA system of FIG. 2A.
Figure 2C:
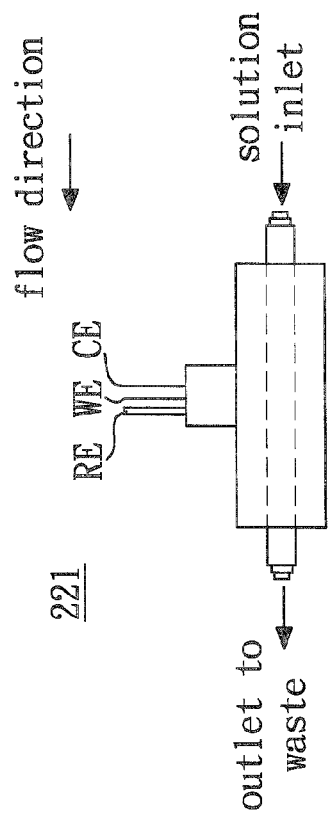

For exemplary purpose, cyclic voltammetric analyses and on-line amperometric measurements shown in FIG. 2A for glucose determination are performed with a CHI611B Electrochemical workstation 222 (Austin, USA) coupled with a specific designed three-electrode flow cell 221 and assisted by the peristaltic pump 223 for buffer delivery. FIG. 2C is a schematic diagram of top-view (left) and the side-view (right) of the specific designed three-electrode flow cell 221. The three-electrode flow cell 221 includes a platinum wire as the counter electrode (CE), a silver/silver chloride electrode (Ag/AgCl) as the reference electrode (RE), and the enzyme electrode prepared by the embodiment of the present invention as the working electrode (WE).

In addition, the stopped-flow sampling subsystem 23 employs a Bio-Rad Model MV-6 6-port injection valve (Hercules, USA) as the six-port injection valve 232. The sampling of the hydrolysate with the stopped-flow was assisted by peristaltic pump 233 and two three-port valves 239A/B. The immobilized enzymatic hydrolysis is performed in a 3 L scale automatic Biotop Process & Equipment BTF-A3L bioreactor (Taichung, Taiwan), which comprises a pH electrode 211 and a temperature probe 212 for respectively controlling the pH and temperature of the content of the bioreactor 21 via a controller 213. Sampling tube 214 is employed for conducting the content of the bioreactor 21.

Notice that in other embodiments, the on-line FIA system 20 can be used to analyze another analyte rather than glucose, and in such cases another enzyme electrode capable of sensing the analyte should be used in the three-electrode flow cell 22. Also notice that the three-electrode flow cell 221 may de designed as two-electrode flow cell.

Quantification of Glucose by HPLC

During the hydrolytic reaction of bamboo chopsticks fiber, the glucose content in the immobilized enzyme hydrolysate was also analyzed on-line simultaneously with HPLC-RI. The sampling time is the same as described before.

Cyclic Voltammetry

The oxidation potential of the enzyme electrode can be found by the cyclic voltammetric (CV) measurement. The scan range of the potential is from 0.0 to 0.7 V with a scan rate of 50 mV s$^{-1}$. Three different glucose standard concentration levels (0 mM, 4 mM, and 10 mM) used for CV measurement are prepared with 0.1 M pH 7.0 NaPB.

Figure 3A:
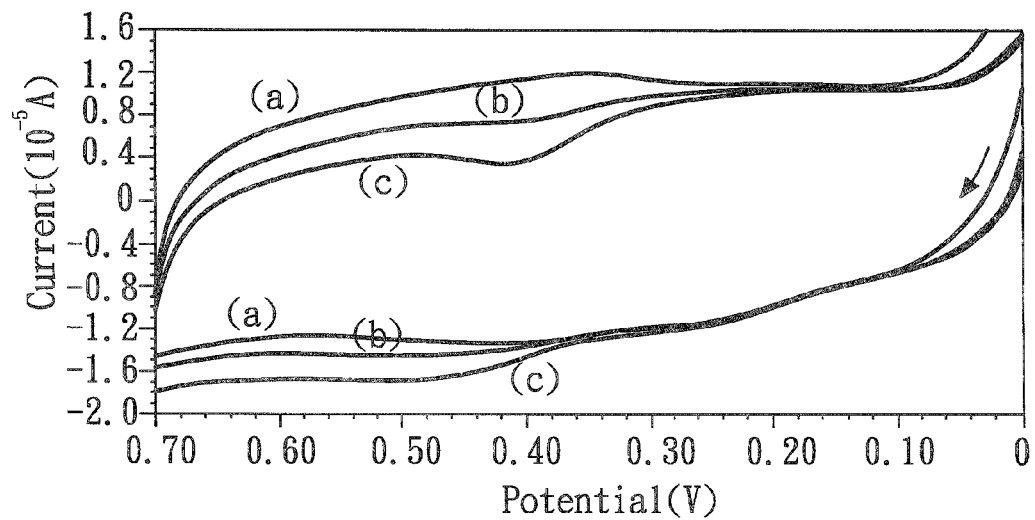
FIG. 3A illustrates the cyclic voltammograms of the enzyme electrode prepared by the embodiment of the present invention with standard glucose concentration of (a) 0 mM, (b) 4 mM, and (c) 10 mM.

FIG. 3A illustrates the cyclic voltammograms of the enzyme electrode prepared by the embodiment of the present invention, where curve (a) denotes 0 mM, curve (b) denotes 4 mM, and curve (c) denotes 10 mM glucose in 0.1 M pH7.0 NaPB, and the arrow denotes the scanning direction.

Comparing these three cyclic voltammograms, it can be observed that both cyclic voltammograms (b) and (c) show an obvious anodic current at 0.45 V and no anodic current was seen in cyclic voltammogram (a). The results proved that the oxidation potential for FcAld is 0.45 V and both FcAld and glucose oxidase were immobilized successfully on the surface of the gold particles modified carbon electrode.

Standard Addition Calibration Method

Standard addition calibration curves of the prepared enzyme electrode are carried out at 35° C. by using standard addition method (Pijanowska et al., 2003). The NaPB was deoxygenated with nitrogen bubbling for 10 minutes before each measurement. The glucose stock solutions (50 mM and 250 mM) are prepared by using a 0.1 M pH 7.0 NaPB and allowed to stand overnight to mutarotate with the glucose before use. The standard addition calibration curve is used to find the sensitivity, limit of detection (LOD), and linear glucose concentration range. To prepare the glucose standard addition calibration curve, eight milliliters of 0.1 M pH 7.0 NaPB were placed into the electrochemical cell as the background solution. Three minutes later, a small volume (2 to 285 μL) of the glucose standard solution is added successively every 1.5 minutes until a concentration of 55.6 mM was reached. The readout current for each standard addition is taken at the last 3 seconds of the standard addition.

Figure 3B:
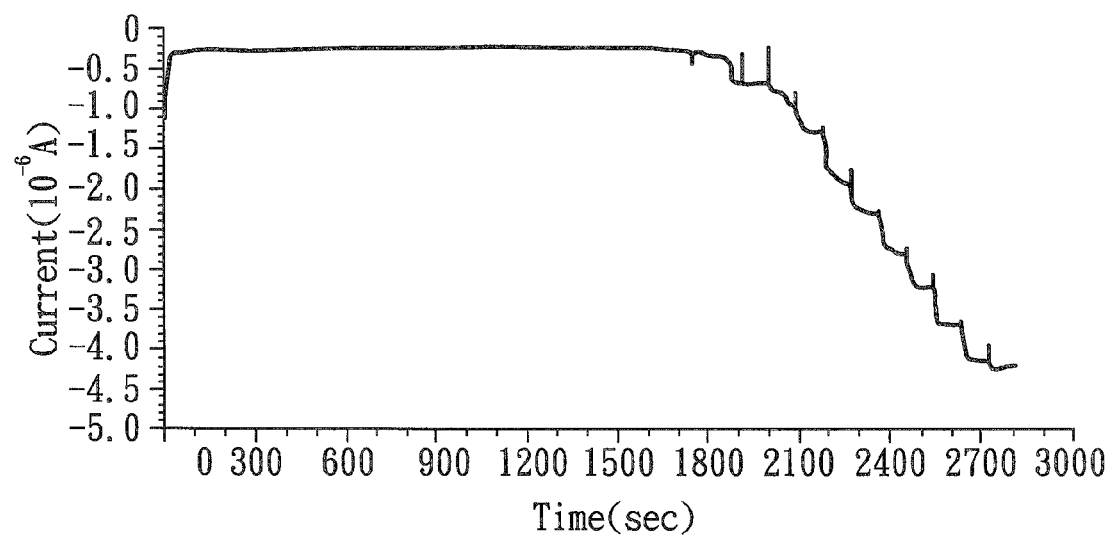
FIG. 3B is the current-time curve of the standard glucose addition of the enzyme electrode prepared by the embodiment of the present invention.

FIG. 3B is the current-time curve of the standard glucose addition of the enzyme electrode prepared by the embodiment of the present invention. The standard addition current-time curve of the enzyme electrode is obtained by the addition of a specific volume of glucose standard solutions into the NaPB as described before. The current change during each glucose standard addition shown in FIG. 3B indicates the extent of glucose oxidation that corresponds to the amount of the added glucose. The current change is not obvious during the time interval 600-1800 seconds due to a small amount of glucose added. But the small current signals can be read by enlarging the part of the diagram.

Figure 3C:
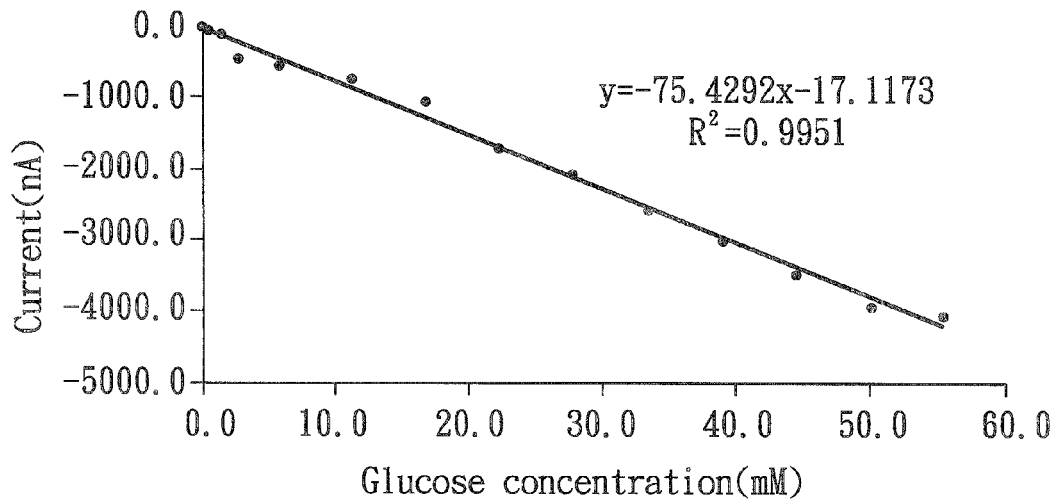
FIG. 3C is the glucose standard addition calibration curve of the enzyme electrode prepared by the embodiment of the present invention.

FIG. 3C is the glucose standard addition calibration curve of the enzyme electrode prepared by the embodiment of the present invention. The glucose standard addition calibration curve is obtained from the linear least-square regression for the current versus the corresponding glucose concentration at each standard addition of FIG. 3B. The result shows that the glucose standard addition calibration curve possesses the widest linear concentration range (0-55.5 mM) with a linearity ($r^2$=0.9951). The best linear concentration range reported in literatures for the glucose standard addition calibration curve is from 0.05 to 26 mM and linearity ($r^2$) of 0.9948 (Tan et al., 2005).

The detection sensitivity of the enzyme electrode is the slope of the standard addition calibration curve in FIG. 3C, 75.4 nA mM$^{-1}$. This is good for the glucose analysis. The LOD of the enzyme electrode prepared by the embodiment is 15.0 μM, which is better than that of those published glucose biosensors made with carbon electrode (Asav and Akyilmaz, 2010; Barsan et al., 2007; Ghica and Brett, 2006; Tsai and Tsai, 2009).

Stability of the Enzyme Electrode

Figure 4:
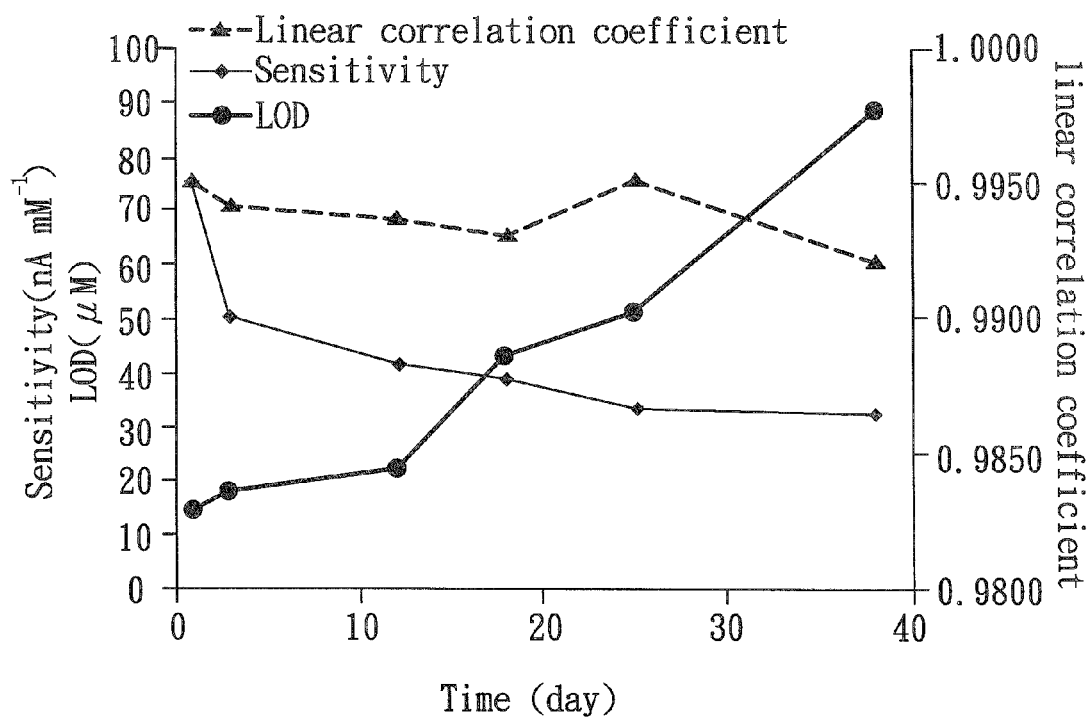
FIG. 4 shows the long-term performance of the enzyme electrode prepared by the embodiment of the present invention (linear correlation coefficient --▲--, sensitivity -♦-, LOD -●-.

FIG. 4 shows the long-term performance of the enzyme electrode prepared by the embodiment of the present invention, where (--▲--) denotes linear correlation coefficient of the glucose standard addition calibration curve, (-♦-) denotes the sensitivity, and (-●-) denotes the limit of detection (LOD). After a 38-day testing period, the sensitivity of the enzyme electrode is lowered to about 32.4 nA mM$^{-1}$ (43%) of the initial sensitivity; however, it still exhibited a good linear concentration range (0-44.4 mM) with a linearity of 0.9922. The LOD of the electrode is varied significantly from about 15 μM to 90 μM. In some literatures, the sensitivity of their electrodes were reduced to 0.15 μA mM$^{-1}$ (50%), 0.20 μA mM$^{-1}$ (69%), 4.86 μA mM$^{-1}$ (85%), or 6.7 μA mM$^{-1}$ (90%) of the initial sensitivity after 10 days or one month period (Asav and Akyilmaz, 2010; Ghica and Brett, 2006; Sun et al., 2008; Yang et al., 2006). Results indicate that the decay of the sensitivity for glucose sensor electrode is an unavoidable issue. However, as long as the electrode has good linearity in some ranges of glucose concentration, the electrode is available for use. Thus, the linear glucose concentration range and the LOD of the electrode are the two most important factors for practical applications.

The Optimal Flow Rate of FIA System for Glucose Analysis

In FIA system, the developed enzyme electrode is the working electrode for the amperometric glucose measurement. The supporting electrolyte solution (0.1 M pH 7.0 NaPB) serves as a carrier solution of the immobilized enzyme hydrolysate. Since the signal produced from the enzyme electrode is affected by the flow rate of the supporting electrolyte solution, the optimal flow rate was studied according to the peak shape of the signal. Different flow rates of 1.0, 1.5, 2.0, 2.5, 3.0 and 4.5 mL min$^{-1}$ were used the experiment.

Figure 5A:
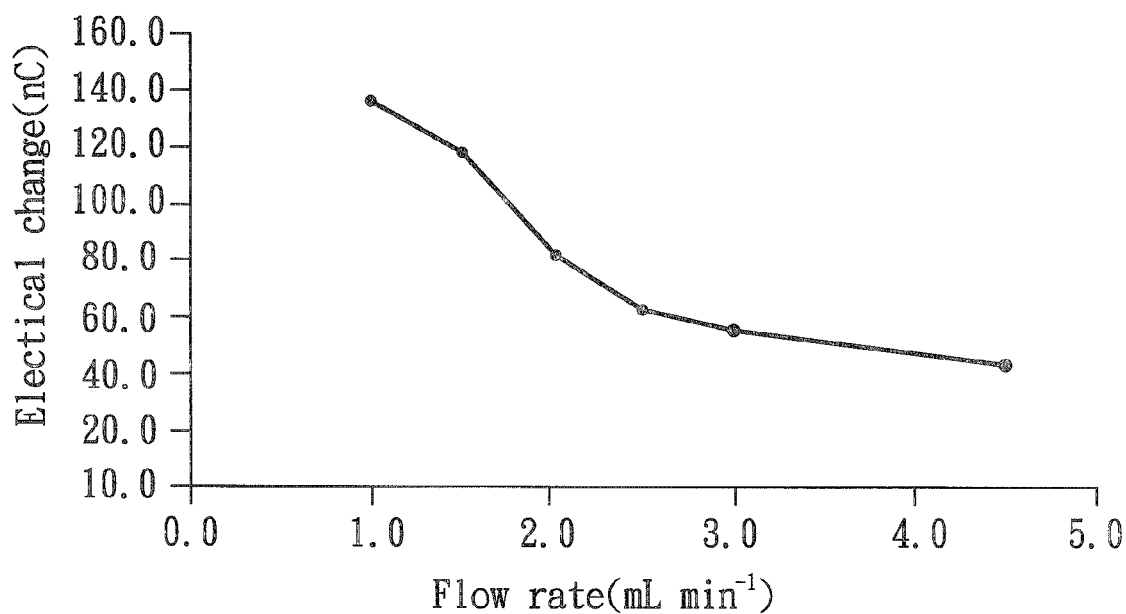
FIG. 5A shows the average response of FIA system for glucose standard solution at different flow rates.
Figure 5B:
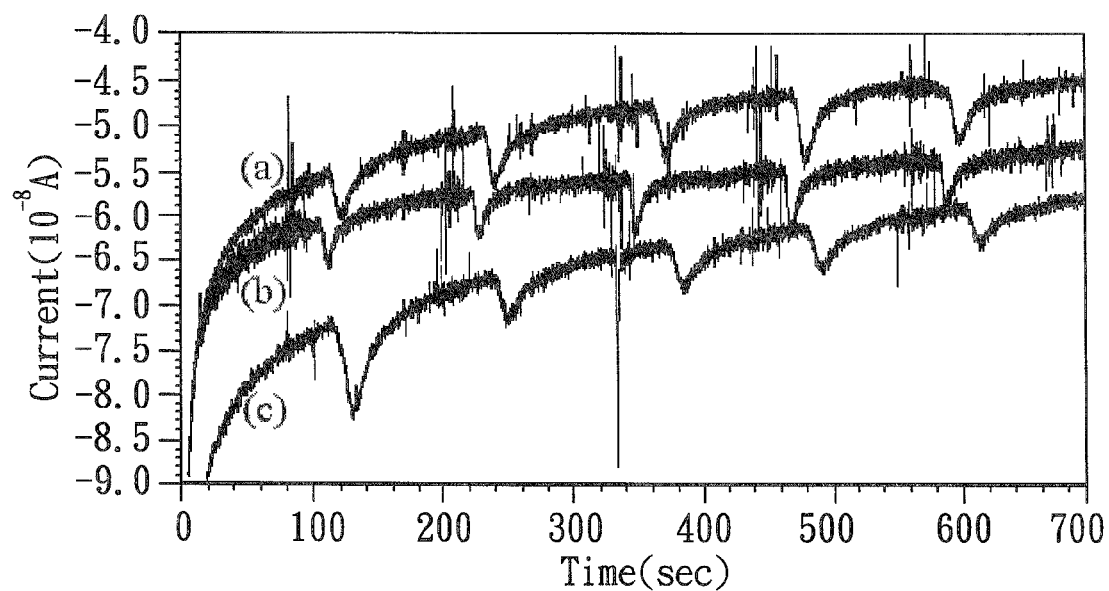
FIG. 5B shows the current of successive five measurements for standard glucose solution under different flow rates of (a) 2.00 mL min$^{-1}$, (b) 1.5 ml min$^{-1}$, (c) 1.0 mL min$^{-1}$.

FIG. 5A shows the average response of FIA system for glucose standard solution at different flow rates. FIG. 5B shows the current of successive five measurements for standard glucose solution under different flow rates, where (a) denotes 2.0 mL min$^{-1}$, (b) denotes 1.5 mL min$^{-1}$, and (c) denotes 1.0 mL min$^{-1}$, and measurements are performed with conditions that applied potential 0.45 V; carrier solution 0.1 M pH 7.0 NaPB; injection volume 50 μL; and glucose concentration 0.2 mM.

FIG. 5A illustrates a decrease of signal with an increasing of flow rate. And it is observed that when the flow rate is larger than or equal to 2.5 mL min$^{-1}$ the signal was too small to be used for the measurement. Although the largest signal (136.3 nC) is with the flow rate of 1.0 mL min$^{-1}$, FIG. 5B tells that the most stable signal to be obtained is with the flow rate of 2.0 mL min$^{-1}$. Therefore, the flow rate 2.0 mL min$^{-1}$ is chosen as the optimum.

Interference for Glucose Analysis with FIA System

The measurement of glucose in a sample with the glucose sensor electrode is usually subject to interferences by other substances, particularly, those carbohydrates of similar structure to glucose. During the hydrolysis, at least three kinds of carbohydrate products including glucose, xylose, and cellobiose are proved to be present in the hydrolysate with the on-line HPLC-RI. However, previous studies (Cheng et al., 2010; Cheng et al., 2006) indicate that some trace sugar products (arabinose, mannose and galactose) should exist in the cellulosic fiber hydrolysate. Therefore, standard glucose solution of 1.66 mM and the standard solution containing 1.66 mM glucose plus the interference carbohydrate of 3.33 mM (Barsan et al., 2007) are prepared and tested separately. The signals of the two solutions obtained with the FIA system were compared to calculate the selectivity coefficient. Table 1 shows the degree of interference for some selected carbohydrates of the developed enzyme electrode of on-line FIA system. It shows the degree of interference (i.e. the selectivity coefficient, $k^c_{glucose,\ interface}$) are all 0% for disaccharide cellobiose and the two pentoses xylose and arabinose. This result indicates that cellobiose, xylose, and arabinose will not show any interference during glucose determination with FIA system. However, for the two hexoses galactose and mannose of similar structure to glucose, the interference is 7% and 5%, respectively.

TABLE 1

| Carbohydrates | Signal ratio[a,b] | Degree of interference (%) | $k^c_{glucose,\ interference}$ |
|---|---|---|---|
| cellobiose | 1.00 ± 0.01 | 0.0 | 0.00 |
| xylose | 1.00 ± 0.01 | 0.0 | 0.00 |
| arabinose | 1.00 ± 0.01 | 0.0 | 0.00 |
| mannose | 1.07 ± 0.01 | 7.0 | 0.07 |
| galactose | 1.05 ± 0.01 | 5.0 | 0.05 |

[a]Number of measurement (n) = 3
[b]Signal ratio = (Total signal)$_{glucose+interference}$/(Signal)$_{glucose}$
[c]$k_{glucose,\ interference}$ = (Signal)$_{interference}$/(Signal)$_{glucose}$ Comparison of Quantitative Results Between Two Analytical Methods The determination of glucose content in the immobilized enzyme hydrolysate has been analyzed on-line by both the FIA glucose enzyme electrode method and the HPLC-RI method. Table 2 lists the quantitative results of the glucose content in the immobilized cellulase hydrolysate of waste bamboo chopsticks fibers by two analysis methods. In Table 2, except for the analysis time at 4 hours the amount of glucose acquired at different hydrolysis times by the on-line FIA glucose sensor electrode method are all higher than those obtained by the on-line HPLC method. It seems that there is systematic error between the two analytical methods. However, considering the interference derived from galactose, mannose, and other unknown substances produced during the hydrolysis for the sensor electrode method and the matrix effect with the HPLC method that uses RI detection and on-line external standard calibration quantification method for glucose analysis, the results shown in Table 2 should be correct. To prove whether there is systematic error between the two analytical methods, these should be tested statistically by linear regression line method (Miller and Miller, 2000).

Figure 6:
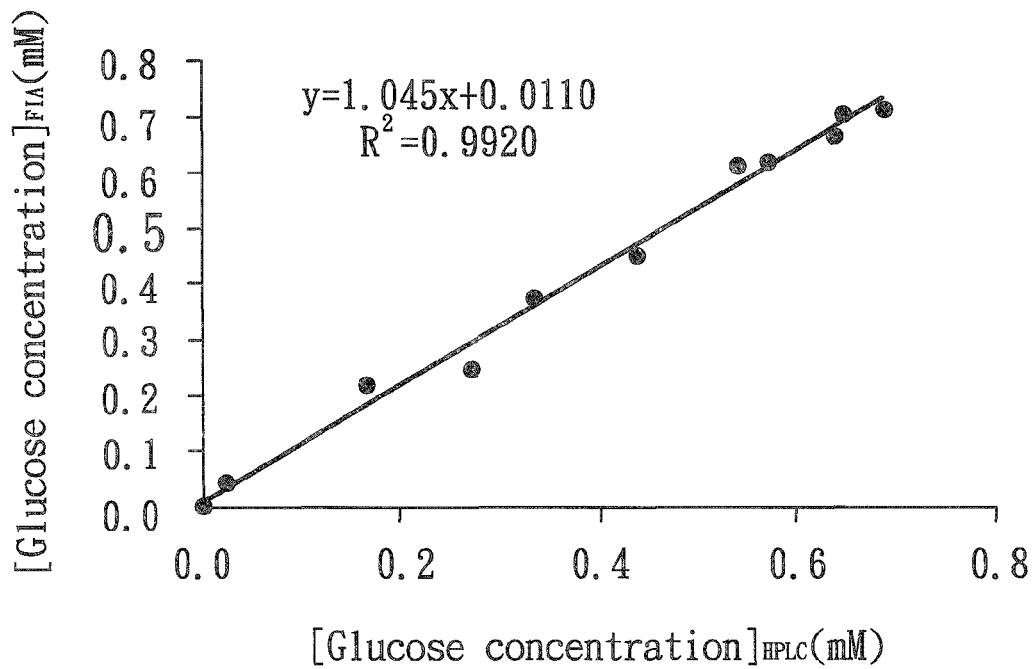
FIG. 6 shows the comparison of quantitative results of glucose content in the immobilized enzyme hydrolysate between the on-line HPLC-RI system and the on-line FIA enzyme electrode system by the statistical regression line method.

FIG. 6 shows the comparison of quantitative results of glucose content in the immobilized enzyme hydrolysate between the on-line HPLC-RI system and the on-line FIA enzyme electrode system by the statistical regression line method. In FIG. 6, each data point represents the paired glucose concentration taken from both analytical methods at one particular sampling time. The linear regression line has a slope of 1.0451 and a y-intercept of 0.0110 with a good linearity ($r^2$) of 0.9920. The calculated 95% confidence interval of the slope is from 0.9744 to 1.1158 which includes the ideal slope of 1.0 and the calculated 95% confidence interval of the intercept is from −0.0019 to 0.0239 which includes 0 (the origin) for a perfect correlated data. Therefore, the results obtained from the two analysis methods are comparable and shows no systematic error between the two analytical methods.

TABLE 2

| | Analysis method | | | |
|---|---|---|---|---|
| | On-line HPLC[a] | | | On-line FIA[a] |
| Reaction time (h) | Cellobiose (mM) | Glucose (mM) | Xylose (mM) | Glucose (mM) |
| 0 | 0.02 | 0.02 | 0.11 | 0.04 |
| 4 | 0.05 | 0.27 | 0.69 | 0.25 |
| 8 | 0.04 | 0.44 | 0.76 | 0.45 |
| 12 | 0.03 | 0.54 | 0.85 | 0.61 |
| 16 | 0.03 | 0.57 | 0.85 | 0.62 |
| 24 | 0.02 | 0.64 | 0.90 | 0.67 |
| 32 | 0.03 | 0.69 | 0.96 | 0.71 |
| 40 | 0.03 | 0.65 | 0.94 | 0.70 |

TABLE 2-continued

| | Analysis method | | | |
|---|---|---|---|---|
| | On-line HPLC[a] | | | On-line FIA[a] |
| Reaction time (h) | Cellobiose (mM) | Glucose (mM) | Xylose (mM) | Glucose (mM) |
| 48 | 0.02 | 0.33 | 0.84 | 0.37 |
| 56 | 0.02 | 0.16 | 0.76 | 0.21 |
| 64 | 0.00 | 0.00 | 0.51 | 0.00 |

[a]Number of measurement (n) = 2

Accordingly, a novel enzyme electrode has been developed by chemically bonding the redox mediator and the glucose oxidase to the electrode that exhibits the widest linear standard calibration concentration range, low LOD value, and long-term stability for glucose measurement. The developed enzyme electrode can be used to form an FIA system through the use of a specific designed three-electrode flow cell and a stopped-flow sampling subsystem. The FIA system can be coupled on-line to a bioreactor to perform the successive on-line determination of the products of the biotransformation. Results of quantitative glucose analysis with the on-line FIA method are comparable to the on-line HPLC-RI method. The analysis precision of this on-line FIA system for glucose determination is below 3.7%.

Figure 7:
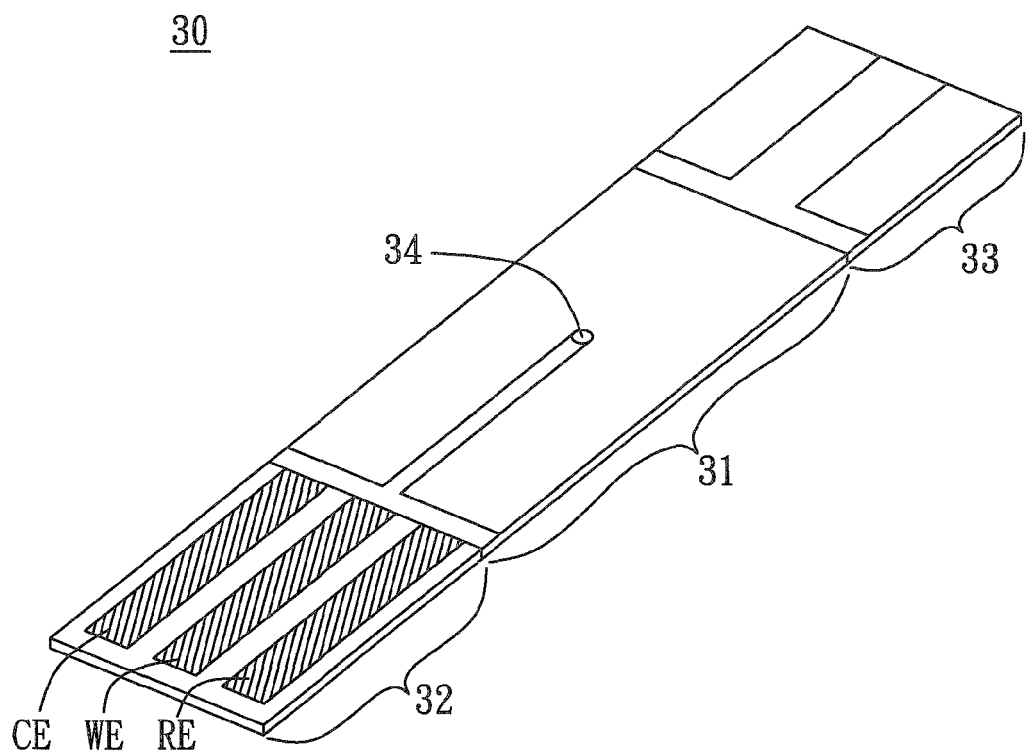
FIG. 7 shows a test strip used by a glucose meter, according to an embodiment of the present invention.

Furthermore, the enzyme electrode produced by the present invention may be used to construct a test strip, which is used and read by a glucose meter to calculate the blood glucose level for diabetics. FIG. 7 shows a test strip 30 used by a glucose meter, according to an embodiment of the present invention. The test strip comprises a capillary section 31, an electrode section 32, and an electrical contact section 33. The electrode section 32 at least comprises a working electrode (WE), a counter electrode (CE), and a reference electrode (RE), and the enzyme electrode prepared by the present invention is employed to function as the working electrode (WE). The capillary section 31 at least includes a capillary opening 34 configured to draw a blood sample through the capillary section and contact with the electrodes of the electrode section 32 via capillary attraction, such that the glucose level of the blood sample can be determined.

The working electrode (WE) of the test strip 30 has at least a portion that is bounded with glucose oxidase and the redox mediator. For example, the whole surface of the working electrode may be deposited with gold, but only a portion, such as the end portion or the middle portion of the gold surface, is modified and bounded with the glucose oxidase and the mediator.

The electrode section 32 is electrically connected with the electrical contact section 33 through wires distributed under the capillary section 31. When testing, the electrical contact section is inserted into the glucose meter and currents generated by the electrode section 32 are read through the electrical contact section 33 to calculate the blood glucose level.

In another embodiment, the electrical contact section 33 may be omitted. In this case, the electrode section 32 is inserted into the glucose meter and current are directly read from the electrode section 32. In addition, the capillary opening 34 may be arranged on the end or side rather than the middle of the capillary section 31.

Conventional glucose test strip is disposable; however, the test strip 30 of the present invention can be reusable since the working electrode, i.e., the enzyme electrode, has excellent long-term stability. For attaining this object, the capillary section 31 may be designed as replaceable, and the electrode section 32 and the electrical contact section 33 are designed as reusable. After a test measurement is completed, the electrode section 32 is immersed into a solution to strip blood sample and products of reaction remained on the electrodes, and then the capillary section 31 is replaced by another fresh capillary section 31 and thus ready for next measurement.

Although specific embodiments have been illustrated and described, it will be appreciated by those skilled in the art that various modifications may be made without departing from the scope of the present invention, which is intended to be limited solely by the appended claims.

What is claimed is:

1. A method for producing an enzyme electrode, comprising:
   providing a substrate with a carbon surface;
   forming a gold surface on the carbon surface and thus forming an electrode;
   modifying the electrode by an amino acid including an amine group, a carboxyl group, and a thiol group in a side chain, wherein the amino acid binds to the gold surface through the thiol group;
   covalently bonding a mediator containing an aldehyde group to the electrode, wherein the aldehyde group of the mediator and the amine group of the amino acid form a Schiff base;
   modifying the electrode by a peptide-coupling reagent with a diimide structure, wherein the central carbon atom of the peptide-coupling reagent binds to the carboxyl group of the amino acid through a nucleophilic reaction and thus form an O-acylisourea intermediate; and
   covalently bonding a glucose oxidase to the electrode, wherein one of the amine groups of the glucose oxidase binds the carboxyl group of the amino acid to form an amide bond by substituting the O-acylisourea intermediate through a nucleophilic substitution reaction.

2. A method for producing an enzyme electrode, comprising:
   providing a substrate with a carbon surface;
   forming a gold surface on the carbon surface and thus forming an electrode;
   modifying the gold surface by a L-cysteine to covalently bond the gold particles of the gold surface and the sulfhydryl group of the L-cysteine, thereby forming a first electrode with a first modified surface;
   covalently bonding a mediator containing an aldehyde group to the amine group of the L-cysteine thus resulting in a Schiff base, thereby forming a second electrode with a second modified surface;
   modifying the second modified surface by a N,N'-dicyclohexylcarbodiimide, a covalent bond being formed through a nucleophilic attachment of the carboxyl group of the L-cysteine to the central carbon atom of the N,N'-dicyclohexylcarbodiimide, thereby forming a third electrode with a third modified surface; and
   contacting the third modified surface with a glucose oxidase, an amide bond being formed between the carboxyl group of the L-cysteine of the third modified surface and the glucose oxidase, thereby forming a fourth electrode with a fourth modified surface.

3. The method as recited in claim 2, wherein the substrate is made of non-metal material.

4. The method as recited in claim 3, wherein the substrate is a pencil lead.

5. The method as recited in claim 4, further comprising coating a carbon paste on the surface of the pencil lead.

6. The method as recited in claim 4, wherein the mediator comprises Ferrocene carboxaldehyde.

7. An enzyme electrode, comprising:
a substrate with a carbon surface;
a gold surface deposited on at least a portion of the carbon surface;
a modified structure chemically bounded with the gold surface and comprising an amino acid including an amine group, a carboxyl group, and a thiol group, wherein the thiol group binds to the gold surface;
a mediator chemically bounded with the modified structure by a Schiff base formed by an aldehyde group of the mediator and the amine group; and
a glucose oxidase chemically bounded with the modified structure by an amide bond formed by the carboxyl group of the modified structure and one of the amine groups of the glucose oxidase through a peptide-coupling reagent with a diimide structure, wherein the central carbon atom of the peptide-coupling reagent binds to the carboxyl group of the amino acid through a nucleophilic reaction and thus form an O-acylisourea intermediate, and one of the amine groups of the glucose oxidase binds the carboxyl group of the amino acid to form the amide bond by substituting the O-acylisourea intermediate through a nucleophilic substitution reaction.

8. A test strip comprising the enzyme electrode of claim 7, wherein the test strip is used for detecting a blood glucose level of a blood sample and comprises an electrode section having a working electrode, a counter electrode, and a reference electrode, and the enzyme electrode is employed to function as the working electrode.

9. The test strip as recited in claim 8, further comprising a capillary section including a capillary opening configured to draw the blood sample through the capillary section and contact it with the electrodes of the electrode section via capillary attraction, such that the glucose level of the blood sample can be determined.

10. The test strip as recited in claim 9, wherein the capillary section is replaceable, and the used capillary section is replaced by another fresh capillary section after the measurement of the blood sample is completed.

11. The test strip as recited in claim 9, wherein the electrode section is electrically connected with an electrical contact section through conductors distributed under the capillary section, and the electrical contact section is inserted into a glucose meter for reading currents generated by the electrode section to measure the blood glucose level.

12. The test strip as recited in claim 11, wherein the electrode section and the electrical contact section are reusable, and the electrode section is immersed into a buffer solution to strip the blood sample and products of reaction remained on the electrodes after the measurement of the blood sample is completed.

13. The enzyme electrode as recited in claim 7, wherein the amino acid is L-cysteine.

14. The enzyme electrode as recited in claim 7, wherein the peptide-coupling reagent is N,N'-dicyclohexylcarbodiimide.

15. The enzyme electrode as recited in claim 7, wherein the mediator comprises Ferrocene carboxaldehyde.

16. An enzyme electrode, comprising:
a substrate structure comprising a pencil lead, a carbon layer covering the pencil lead, and a gold layer covering the carbon layer; and
a modified structure chemically bounded with the gold layer and comprising a L-cysteine to bind a glucose oxidase and a mediator containing an aldehyde group, wherein an Au-S covalent bond is formed between the gold layer and the L-cysteine, a covalent amide bond is formed between the L-cysteine and the glucose oxidase, and a carbon-nitrogen double bond is formed between the L-cysteine and the mediator.

17. A test strip comprising the enzyme electrode of claim 16, wherein the test strip is used for detecting a blood glucose level of a blood sample and comprises an electrode section consisted of a working electrode, a counter electrode, and a reference electrode, and the enzyme electrode is employed to function as the working electrode.

18. The test strip as recited in claim 17, further comprising a capillary section and an electrical contact section, wherein the capillary section includes a capillary opening configured to draw the blood sample through the capillary section and contact it with the electrodes of the electrode section via capillary attraction, the electrode section is electrically connected with the electrical contact section through conductors distributed under the capillary section, and the electrical contact section is inserted into a glucose meter for reading currents generated by the electrode section to measure the blood glucose level.

19. The test strip as recited in claim 18, wherein the capillary section and the electrical contact section are replaceable, and the tested capillary section is replaced by another fresh capillary section after the measurement of the blood sample is completed.

20. The enzyme electrode as recited in claim 16, wherein the mediator group comprises Ferrocene carboxaldehyde.

* * * * *